(12) United States Patent
Malfroy-Camine

(10) Patent No.: US 6,703,019 B1
(45) Date of Patent: Mar. 9, 2004

(54) CATIONIZED ANTIBODIES AGAINST INTRACELLULAR PROTEINS

(76) Inventor: Bernard Malfroy-Camine, 67 Crosby St., Arlington, MA (US) 02174

( * ) Notice: Subject to any disclaimer, the term of this patent is extended or adjusted under 35 U.S.C. 154(b) by 1668 days.

(21) Appl. No.: 08/931,666

(22) Filed: Sep. 17, 1997

Related U.S. Application Data

(63) Continuation of application No. 08/137,183, filed as application No. PCT/US92/03566 on Apr. 30, 1992, which is a continuation of application No. 07/693,872, filed on Apr. 30, 1991, now abandoned.

(51) Int. Cl.$^7$ .............................................. A61K 39/42
(52) U.S. Cl. ............................... 424/148.1; 435/339.1; 435/70.21; 424/141.1; 424/142.1; 424/160.1
(58) Field of Search ........................... 424/133.1, 141.1, 424/142.1, 148.1, 160.1, 188.1; 435/70.21, 172.2, 328, 339.1; 530/387.3, 388.35, 389.4, 389.6

(56) References Cited

U.S. PATENT DOCUMENTS

| | | | |
|---|---|---|---|
| 5,004,697 A | 4/1991 | Pardridge | 436/547 |
| 5,130,129 A | 7/1992 | Pardridge | 424/85.8 |

OTHER PUBLICATIONS

Barone, et al., "Reactivity of *E. coli*–Derived Trans–Activating Protein of Human T Lymphotropic Virus Type III With Sera From Patients with Acquired Immune Deficiency Syndrome," *J. Immunol.* 137(2):669–673, Jul. 15, 1986.*

Abrams, et al., "Optimal Strategies for Developing Human–Human Monoclonal Antibodies," *Meth. Enzymology* 121: 107–119, 1986.*

Fahey et al. "Status of Immune–Based Therapies in HIV Infection and AIDS," *Clin. Exp. Immunol.*,88: 1–5, 1992.*

Fox, J.L., "No Winners Against AIDS,", *BiolTechnology* 12:128, Feb. 12, 1994.*

Triguero et al., "Blood Brain Barrier Transport of Cationized Immunoglobulin G: Enhanced Delivery Compared to NativeProtein," *Proc.Natl.Acad Sci.,USA.* 86: 4761–4765, Jun. 1989.*

Basu et al., "Degradation of Cationized Low Density Lipoprotein and Regulation of Cholesterol Metabolism in Homozygous Familial Hypercholesterolemia Fibroblasts," *PNAS* 73 (9) : 3178–3182 (Sep. 1976).

Shen, Wei–Chiang and Ryser, Hugus J.–P., "Conjugation of Poly–L–lysine to Albumin and Horseradish Peroxidase: A Novel Method of Enhancing the Cellular Uptake of Proteins," *PNAS* 75 (4) : 1872–1876 (Apr. 1978).

Kumagai et al., "Absorptive–mediated Endocytosis of Cationized Albumin and a β–Endorphin–cationized Albumin Chimeric Peptide by Isolated Brain Capillaries," *J. Biol. Chem.* 262 (31) : 15214–15219 (Nov. 5, 1987).

Pardridge et al., "Transport of Histone through the Blood–brain Barrier," *J. Pharm. Exp. Ther.* 251 (3) : 821–826 (1989).

Brake et al., "Characterization of Murine Monoclonal Antibodies to the tat Protein from Human Immunodeficiency Virus Type 1," *Journal of Virology* 64 (2) : 962–965 (Feb. 1, 1990).

Pardridge et al., "Receptor–Mediated Peptide Transport through the Blood–Brain Barrier," *Endocrine Rev.* 7 (3) : 314–330 (1986).

* cited by examiner

*Primary Examiner*—James Housel
*Assistant Examiner*—Emily Le

(57) ABSTRACT

The subject application discloses methods and compositions for the targeted detection and/or inhibition of an intracellular protein in a cell by contacting the cell with a cationized antibody which reacts specifically with the intracellular protein. An example of an intracellular protein which can be inhibited in this manner is the Tat protein which is encoded by the HIV-1 virus.

15 Claims, 2 Drawing Sheets

CATIONIZED ANTIBODIES AGAINST INTRACELLULAR PROTEINS

Continuation of application Serial No. 08/137,183 filed Mar. 21, 1994 now abandoned, which is the US National phase of PCT/US92/03566 filed Apr. 30, 1992 which is a continuation of 07/693,872 filed Apr. 30, 1991 now abandoned.

BACKGROUND OF THE INVENTION

Members of the lentivirus family, which includes Human Immunodeficiency Virus type 1 (HIV-1), are pathogenic retroviruses that induce chronic, degenerative diseases in their animal hosts. The genomic organization and regulatory mechanisms of the lentivirus family have been found to be more complex than those of other member of the retrovirus family. For example, the genome of HIV-1 encodes the virion proteins Gag, Pol and Env which are common to all replication competent retroviruses, two additional proteins which are necessary for virion morphogenesis and maturation (Vif and Vpu), a protein of unknown function (Vpr), and three nonstructural regulatory proteins (Tat, Rev, and Nef).

The Tat and Rev gene products are trans-activating proteins which regulate HIV-1 gene expression by specific interaction with structured viral RNA target sequences. Because of their importance as potential targets for chemotherapeutic intervention in HIV-induced disease, these trans-activators have been the subject of intense scientific scrutiny.

In addition to the lentiviruses, almost all DNA viruses encode transcriptional trans-activators of viral gene expression. For example, human T cell leukemia virus type 1 (HTLV-1) encodes a transcriptional activator termed Tax, which like the HIV-1 Tat protein acts to greatly amplify viral gene expression. HTLV-1 also encodes a trans-activator, termed Rex, which is required for the expression of the incompletely spliced mRNAs that encode the HTLV-1 Gag, Pol and Env gene products. Recent studies have shown that HTLV-1 Rex protein can functionally replace the HIV-1 Rev polypeptide and rescue replication of a Rev deficient HIV-1 provirus.

Although such intracellular proteins have been recognized as potential targets for intervention, efforts toward this end have been unsuccessful. An effective method for targeting and inactivating such intracellular proteins would be broadly applicable.

SUMMARY OF THE INVENTION

The subject invention relates to a method for targeting an intracellular protein for interaction with an antibody in a cell by contacting the cell with a cationized antibody which binds specifically to the intracellular protein. The specific binding of the cationized antibody to the intracellular protein can be used to accomplish a variety of goals. For example, the binding of the antibody to the intracellular protein can be used to interfere with the activity of the intracellular protein. This is particularly important when the activity of the intracellular protein has a deleterious effect on the host cell. This is the case, for example, with the HIV-1 encoded Tat protein.

Alternatively, the specific binding of the cationized antibody to the intracellular protein can be used in a method for detecting the presence of a particular intracellular protein in a cell. For such an application, the cationized antibody would be labeled with a detectable reporter group.

The methods of the invention are applicable both in vivo for immunotherapeutic or diagnostic uses, and in vitro for research and diagnostic use. A preferred in vivo immunotherapeutic method can be used for treating an individual infected by a virus, for example, HIV-1. An effective amount of a cationized antibody in a pharmaceutically acceptable formulation is administered to the individual.

The methods and compositions disclosed in the subject application offer a new and effective approach for the targeting of an intracellular protein which is based on the discovery that cationized proteins are not necessarily sequestered in intracellular vesicles when taken up by a cell, contrary to the teaching of the prior art.

DETAILED DESCRIPTION OF THE INVENTION

Figure 1:
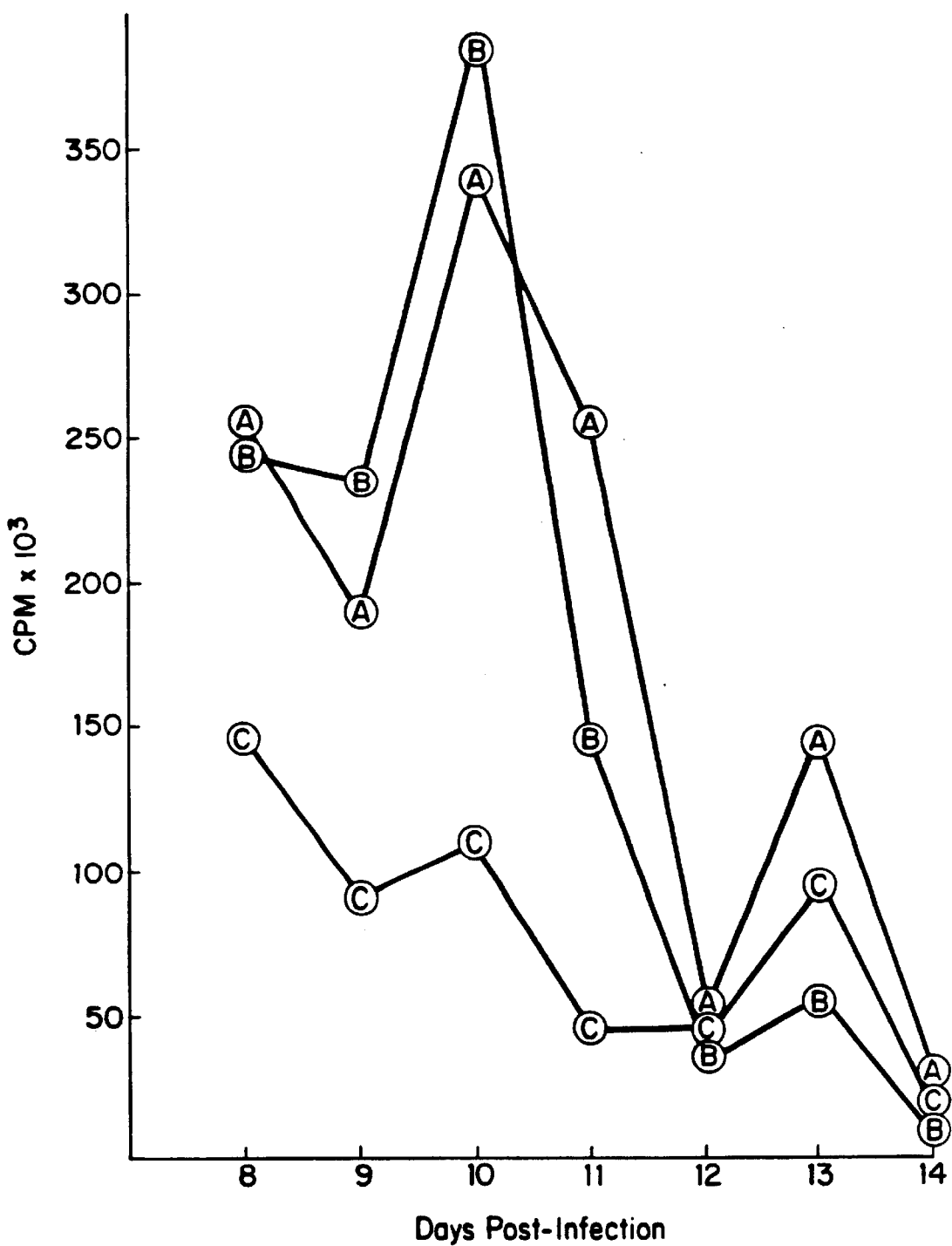
FIG. 1 represents results from a reverse transcriptase activity assay.

Applicant's invention is based on the discovery that a cationized antibody specific for the HIV-1 encoded Tat protein effectively inhibits replication of the HIV-1 virus when taken up by infected cells. This finding was surprising in light of the prior art teaching (reviewed briefly below) that cationized proteins are sequestered in intracellular compartments. If the cationized anti-Tat antibodies were sequestered in intracellular vesicles, as the prior art suggested, the antibodies would not come into contact with the Tat protein which is produced in the cytoplasm and transported to the nucleus.

It is well known in the art that the passage of small polar molecules across the plasma membrane of a cell is mediated by transport proteins. However, these transport proteins cannot transport macromolecules such as proteins, polynucleotides, or polysaccharides. The mechanism by which a cell ingests or secretes such macromolecules involves the sequential formation and fusion of membrane-bound vesicles. For example, ingestion involves the progressive enclosure of the macromolecule by a small portion of the plasma membrane, which first invaginates and then pinches off to form an intracellular vesicle containing the macromolecule. Secretion of macromolecules occurs by a similar mechanism except that an intracellular vesicle is formed which subsequently fuses with the cell membrane thereby releasing the encapsulated macromolecules into the intracellular fluid. Ingestion and secretion by this mechanism are referred to as endocytosis and exocytosis, respectively.

An important aspect of this transport mechanism is that the secreted or ingested macromolecules are sequestered in vesicles. Thus, proteins taken up by a cell by endocytosis do not mix with most of the other macromolecules or organelles in the cytoplasm. The vesicles are designed to fuse only with specific membranes, causing a directed transfer of macromolecules between the outside and inside of the cell.

More specifically, the endocytic cycle begins at specialized regions of the plasma membrane called coated pits. The lifetime of the coated pits is short. Within about a minute after formation, the coated pits invaginate into the cell and pinch off to form coated vesicles. The short-lived coated vesicles then shed their coat and fuse with endosomes. The fate of macromolecules sequestered within endosomes is limited to three possibilities: 1) transport to the lysosome for degradation; 2) recycling of the macromolecule to the same plasma membrane domain from which it came; or 3) transcytosis to a different domain of the plasma membrane. Recycling and transcytosis is mediated by a transport vesicle which buds off from the endosome and carries the macromolecule to its predetermined destination at the plasma membrane.

Cationization of proteins is known, in general, to enhance their cellular uptake. The prior art teaches that the uptake of cationized proteins is by endocytosis. As discussed above, proteins which are taken up by this method are sequestered in intracellular compartments.

For example, in a study focusing on the uptake of cationized horseradish peroxidase, Thyberg et al. (*Eur J. Cell Biol.* 25: 308–318 (1981)) reported that the cationized protein was taken up by endocytosis and sequestered in intracellular compartments. Specifically, the authors state in the abstract that the cationized protein was internalized via membrane folds and transferred not only to lysosomes but also to the Golgi complex.

Another publication which reinforces the teaching in the prior art that cationized antibodies are taken into cells by endocytosis is a review article by William Pardridge (*Endocrin. Rev.* 7: 314–330 (1986)). The author states on page 318 that "[t]he transcytosis process is believed to involve three major steps: (1) endocytosis at the lumenal membrane or blood side of the BBB (blood brain barrier); (2) diffusion through the endothelial cytoplasm, presumably in non-clathrin-containing smooth vesicles; and (3) receptor-mediated exocytosis at the antilumenal membrane or brain side of the BBB.

The above-cited publications are representative of numerous scientific articles which suggest that cationized proteins are taken up by endocytosis and sequestered in intracellular compartments. It is against this backdrop of prior art teaching that Applicant's invention stands in relief.

Cationization Generally

Antibodies are proteins which have both positive and negative charges with the number of each depending upon the pH of the antibody solution. The pH at which the positive and negative charges are equal is called the isoelectric point (pI). Techniques for measuring the pI of a given antibody or protein are well known and generally involve isoelectric focusing according to conventional electrophoretic procedures. Most antibodies have an isoelectric point of between about 5 to 6.

The relatively low isoelectric point of antibodies is due to the presence of carboxyl groups on the surface of the antibodies. Cationization involves substituting basic groups in place of a sufficient number of surface carboxyl groups to increase the PI of the antibody to between 8.0 to 11.0. The optimal pI within this range is determined empirically. For example, as shown in the Exemplification which follows, antibodies can be cationized to varying degrees (resulting in a spectrum of pIs within the range defined above) and these can be tested individually for effectiveness in an appropriately designed assay.

Cationization of the antibody can be carried out according to any of the known procedures for modifying surface carboxyl groups on proteins with basic cations. Preferred cationization agents include amine compounds such as hexamethylenediamine and related amine compounds. Hexamethylenediamine is the preferred cationization agent because it is widely available and the techniques for its use in cationizing proteins are well known. The amount of cationizing agent and the conditions for reaction with the antibody can be varied so long as the final cationized antibody has a pI within the above-mentioned range preferred for transport into a cell.

Although hexamethylenediamine is the preferred compound for use in cationizing antibodies, other cationizing agents are also useful. For example, ethylene diamine, N,N-dimethyl-1,3-propanediamine, putrescine or polylysine may be used. Cationization is catalyzed by carboxyl activation using N-ethyl, $N^1$(3-dimethyl-aminopropyl) carbodiimide hydrochloride (EDAC) as a preferred.compound using the method described by Hoar and Koshland (*J. Biol. Chem.* 342: 2447–2453 (1967)).

In order to prevent reductions in the immunoreactivity of an antibody during cationization, the antibody can be prebound to the antigen of interest prior to cationization. This prebinding with antigen effectively blocks the immunoreactive sites on the antibody and prevents them from being cationized. After cationization is complete and the pI of the antibody has been raised to the desired level between about 8.0 to 11.0, the cationized antibody is then treated to unbind the antigen from the antibody. The unbinding is accomplished according to well known procedures where the antibody-antigen complex is treated with an acid to break the antibody-antigen bond. The antibody is then recovered by column chromatography or other conventional separation and recovery techniques.

The cationized antibodies of this invention are preferably, but not necessarily, monoclonal antibodies. Methods for the preparation of monoclonal antibodies are well known in the art. Cationized polyclonal antibodies are also within the scope of the invention.

Target Proteins

The Exemplification which follows, clearly demonstrates the effectiveness of Applicant's method for the treatment of cells infected by the HIV-1 virus. A monoclonal antibody specifically reactive with the HIV-1 encoded Tat protein was cationized using conventional methods. The Tat protein is a trans-activating protein which regulates HIV-1 gene expression through a mechanism which depends on the specific recognition of structured viral RNA target sequences. The primary role of the Tat protein is to act as a highly effective trans-activator of HIV long terminal repeat (LTR)-dependent transcription.

The scope of the subject invention is not limited, however, to targeting the HIV-1 encoded Tat protein. One skilled in the art could predict, based on the teaching of the specification, that cationized antibodies could be used to target any intracellular protein. Intracellular proteins are those which are contained within the cellular membrane. This distinguishes those proteins which are exposed, at least partially, to the exterior of the cell. Such proteins, which are at least partially exposed to the exterior of the cell, do fall within the scope of this invention prior to transport to the cell surface. Also, several such proteins (e.g. proto-oncogenes) have a functional intracellular domain which can be blocked using cationized antibodies directed against such domains. The scope of this invention includes the use of cationized antibodies which interact specifically with an intracellular portion of such transmembrane proteins.

As discussed in the Backaround of the Invention section, retroviruses (in particular the lentivirus branch) and DNA viruses encode a variety of trans-acting intracellular proteins which could be targeted by the methods described herein. These include, for example, the HIV-1 Rev protein and the HTLV-1 Rex protein.

One skilled in the art would predict that any intracellular protein, particularly a non-compartmentalized cytoplasmic protein, could be targeted as described herein. It is Applicant's fundamental teaching that cationized antibodies can interact with cytoplasmic proteins that makes possible the targeting of such proteins. Given this teaching, one skilled in the art would predict with a high degree of certainty that such antibodies would complex with the target protein under physiological conditions.

Methods of the Invention

In one aspect, the methods of the invention relate to the use of a cationized antibody, for targeting an intracellular protein for interaction with an antibody in a cell. There are a variety of reasons for targeting an intracellular protein for interaction with an antibody. For example, if the intracellular protein plays a role that is deleterious to the host cell, it may be desirable to interfere with.the activity of the intracellular protein. The introduction of a cationized antibody which binds specifically to the intracellular protein can be effective in this regard as is shown clearly by the Exemplification which follows.

As is well known by those skilled in the art, proteins exhibit a very high degree of specificity. This is true of all classes of proteins including, for example, enzymes, structural proteins, and regulatory proteins. The binding of a cationized antibody to an intracellular protein can interfere with the activity of the intracellular protein in a multitude of ways. For example, interference can be effected by binding to the intracellular protein in such a way that an active site on the intracellular protein is blocked. Inhibition can result from interference by the antibody with conformational changes in the intracellular protein which are essential for the functioning of the intracellular protein. Inhibition could also result from the effect of antibody binding on intracellular protein transport. For example, if the intracellular protein is a DNA binding protein, the binding of the cationized antibody to the protein may interfere with the transport of the intracellular protein to the nucleus. Many potential mechanisms are conceivable but the subject invention is not limited by any mechanistic theory of inhibition.

The practice of this method is technically straightforward. All that is required is a cationized antibody specifically reactive with the intracellular protein of interest, and an assay for the activity of the intracellular protein of interest. Thus, the method is applicable to a wide array of intracellular proteins.

A specific example of this method is provided in the Exemplification which follows relating to the HIV-1 encoded Tat protein. The Tat protein is a regulatory protein (specifically a trans-activator) which stimulates transcription of HIV-1 encoded proteins. Antibodies specifically reactive with this protein are commercially available. A sensitive assay for monitoring Tat activity, the reverse transcriptase assay, is also well known. It is clearly demonstrated by the reverse transcriptase assay that cationized anti-Tat antibodies interfere with the normal function of the Tat protein in HIV-1 infected cells.

Interference in this context, therefore, means that the cationized antibody binds to the Tat protein thereby reducing the level of HIV-1 transcription relative to the level of transcription which would be detected in the absence of the cationized anti-Tat antibody. Specifically, it is shown in FIG. 1 that at the peak of HIV-1 activity, the effect of cationized anti-Tat antibody introduction is a decrease of between 70–80% in reverse transcriptase activity.

Another reason for targeting an intracellular protein for interaction with an antibody, aside from the inhibitory goal described above, is for purposes of detection. Antibodies can be labeled with a variety of detectable reporter groups by conventional methods. Antibodies labeled with such reporter groups are introduced into cells to be assayed for the presence of an intracellular protein of interest and the detection of specifically bound antibody is detected by appropriate means.

Such methods are useful both in vivo and in vitro. In vivo uses include both therapeutic and diagnostic applications. A cationized antibody can be administered to an individual, preferably intravenously. Compositions for intravenous administration are well known in the art. For example, the cationized antibody can be suspended in a buffered solution, preferably at a concentration of about 20% or less. Preferably, this solution has an ionic strength and pH sufficient to maintain the monomer content of the immunoglobulin at a maximum level. The pH of the solution is preferably adjusted to about 3.5 to 5.0 by the addition of a physiologically acceptable acid (e.g. acetic acid).

Following the pH adjustment, the composition is treated to reduce its ionic strength and also to maintain the monomer content of the immunoglobulin at maximal levels. The preparation is then treated to render it isotonic, i.e., to render it compatible with physiological conditions or render it physiologically acceptable upon injection. In this respect it is important to note that isotonicity must be achieved without raising the ionic strength of the preparation. This end is achieved by adding to the preparation an amount of an amino acid such as glycine or the like, or a carbohydrate such as maltose, dextrose, fructose, or the like, or a sugar alcohol such as mannitol, sorbitol, etc., or mixtures thereof. Thus, for example, the preparation may be mixed with about 10% maltose (on a weight to volume basis) to render the preparation isotonic.

The cationized anti-Tat antibody described in the Exemplification and prepared for intravenous administration can be administered to an individual who is infected by the HIV-1 virus. The assay conditions described in the Exemplification mimic, to a large extent, physiological conditions. Therefore, one skilled in the art would predict with a high degree of certainty that cationized antibodies administered intravenously would be taken up by infected lymphocytes and that these antibodies would interfere with replication of the HIV-1 virus in vivo.

In an immunodiagnostic method in vivo, the technique would be similar. However, the cationized antibody would be labeled with a detectable reporter group which is safe for introduction into a human. Such reporter groups are known to those skilled in the art.

In vitro, the methods of the invention can be used diagnostically, or for any other appropriate research purpose. In a preferred diagnostic method, the cationized antibody is labeled with a fluorescent reporter group, and the cells are analyzed for the presence of the intracellular protein of interest by flow cytometry.

The Exemplification which follows demonstrates the power of the claimed methodology for use in basic research. Many disease states, including for example, viral infection and cancer, are characterized by the presence of a particular intracellular protein and are commonly studied on human cells grown in culture.

EXAMPLES

Example 1

It has been previously shown that purified Tat protein added to human lymphocyte cell cultures is rapidly taken up by the cells and that internalized Tat, in an as yet unidentified manner, facilitates blocking of lymphocyte proliferation. As discussed in the present Example, the activity of the cationized anti-Tat antibody was tested first in a lymphocyte proliferation assay, and then its effect on lymphocytes infected by the HIV-1 virus was assessed.

Cationized Antibody Preparation

Monoclonal antibodies reactive with the Tat protein encoded by the HIV-1 virus were obtained from American Biotechnologies, Inc. (Cambridge, Mass.). The antibodies reactive with the Tat protein were cationized, to varying degrees, by conventional methods (see e.g. Kumagai et al., J. Biol. Chem. 262: 15214–15219 (1987); Pardridge et al., Biochem, Biophys, Res, Commun, 146: 307–313 (1987)).

To cationize the anti-Tat antibodies to varying degrees, five separate reaction mixtures were prepared, each containing approximately 1 mg of anti-Tat antibody. The anti-Tat reaction mixtures (designated anti-Tat #1 through anti-Tat #5) contained 5.2 µmoles N-ethyl-N'-3-(dimethylaminopropyl) carbodiimide hydrochloride. In addition, anti-Tat #1 through anti-Tat #5 contained 54, 27, 13, 6 and 2.7 µmoles of hexamethylenediamine, respectively. The effect of varying the concentration of the cationizing reagent is varying degrees of cationization from extensive (#1) to mild (#5).

The cationization reactions were carried out in the absence of the Tat protein and therefore the affinity of the cationized antibody for the Tat protein was assessed by an ELISA binding assay. The Tat protein used in the binding assay and in the Sup T1 assays described below was also obtained from American Biotechnologies. In the ELISA assay the cationized antibodies were found to have retained only about 5–10% of the Tat binding affinity relative to the native antibody.

Lymphocyte Proliferation Assay

Lymphocyte proliferation studies were conducted using the well known Sup T1 cell line. The Sup T1 cell line is a CD4 bearing cell line which can be infected by HIV-1 in vitro. Tat protein (10 µg/ml) was added to a Sup T1 cell culture ($2 \times 10^2$ cells/well) for 8 hours, and $^3$H thymidine was included in the culture for the last 2 hours of the 8 hour period. Incorporation of the labeled nucleotide is a function of cell growth and division. The addition of Tat to the growth medium resulted in an average decrease of 70% in lymphocyte proliferation. As shown in Table 1, below, the average counts per minute for 4 separate experiments incorporated by control cells (not exposed to Tat) was 35,691, whereas the culture exposed to the Tat protein incorporated 10,057 counts per minute. This result is consistent with prior reports and confirms the validity of the Sup T1 lymphocyte proliferation assay.

Cationized anti-Tat antibody preparations (#1 through #5) were tested for their effect on lymphocyte proliferation in the Sup T1 assay. Approximately $2 \times 10^5$ cells were exposed to 5 µg/ml of anti-Tat antibody for 10 minutes, washed 4 times with PBS and then cultured with or without the addition of Tat protein (10 µg/ml). The cells were cultured for a total of 8 hours, including a 2 hour pulse with 1 µCi $^3$H thymidine. The experiment was conducted 4 times and the averages are set forth below in Table 1.

TABLE 1

| Condition | CPM (Std. Dev.) |
| --- | --- |
| Control | 35,691 (1,036) |
| Tat (10 µg/ml) | 10,057 (974) |
| anti-Tat #1 + Tat | 22,643 (1133) |
| anti-Tat #2 + Tat | 27,464 (796) |
| anti-Tat #3 + Tat | 31,962 (1079) |
| anti-Tat #4 + Tat | 29,873 (1236) |
| anti-Tat #5 + Tat | 23,649 (941) |
| anti-Tat #6 + Tat | 12,314 (1092) |
| native anti-Tat + Tat | 11,982 (879) |

In Table 1, anti-Tat #6 represents a blind control (i.e. native antibody added with Tat protein to the Sup T1 cell culture). Native antibody refers to non-cationized anti-Tat antibody. The addition of native anti-Tat antibody had no blocking effect, even at a concentration of 30 micrograms/ml. It should also be noted that cells treated with anti-Tat alone demonstrated thymidine uptake at levels similar to that observed in control cells in all experiments performed.

The results clearly demonstrate the ability of the cationized antibody to counteract the anti-proliferative effect of Tat in the Sup T1 assay. As shown above, anti-Tat #3 was the most effective of the antibodies tested in terms of its ability to block the effect of the Tat protein. This shows that the most extensive degree of cationization does not necessarily correlate with optimal activity. The addition of Tat alone resulted in an average decrease of approximately 70% in lymphocyte proliferation. The decrease in lymphocyte proliferation observed when Tat was added with anti-Tat #3 was only approximately 10%.

Another set of experiments was performed with anti-Tat #3, in varying concentrations, in order to generate a dose response curve. The protocol used was identical to that outlined above except the antibody concentration was varied as specified. The results from this experiment are set forth in Table 2.

TABLE 2

| Condition | CPM (Std. Dev.) |
| --- | --- |
| Control | 10,729 (947) |
| Tat (10 µg/ml) | 3,666 (251) |
| anti-Tat #3 (10 µg/ml) + Tat | 9,982 (367) |
| anti-Tat #3 (5 µg/ml) + Tat | 8,619 (510) |
| anti-Tat #3 (1 µg/ml) + Tat | 7,936 (865) |
| anti-Tat #3 (0.1 µg/ml) + Tat | 6,570 (425) |
| anti-Tat #3 (0.01 µg/ml) + Tat | 10,952 (486) |

A rough time course has indicated that the effects of anti-Tat, using a 10 minute exposure before washing, are not detectable for a 24 hour culture.

Effect of Anti-Tat on HIV-1 Infected Cells

To determine the effect of cationized anti-Tat antibodies on HIV-1 infected cells the Sup T1 cell line was again employed. Sup T1 cells were cultured with low titer HIV-1 virus until evidence of ongoing infection was observed. By day 8 this evidence was observed with the appearance of larger and giant cells. On day 8 an aliquot of infected cells were treated with 5 µg/ml cationized anti-Tat antibody, and another aliquot was contacted with non-cationized anti-Tat antibody (10 µg/ml). The antibody was added to the cells and remained in the culture. At 24 hour intervals the cultures were harvested and aliquots removed for conventional reverse transcriptase analysis. The remaining cells were washed and resuspended in fresh media with 5 µg/ml cationized anti-Tat antibody or 10 µg/ml non-cationized antibody. The experiment was conducted for 7 days, at which time all of the aliquots were analyzed for reverse transcriptase activity.

The results from this experiment are shown in FIG. 1. Curve A represents a control culture to which no antibody was added. Curve B represents label incorporation in the presence of native anti-Tat. Curve C represents label incorporated in the presence of cationized anti-Tat #3.

Each curve exhibits the characteristic bell-shaped distribution. Reverse transcriptase activity for the untreated control on day 8 was approximately 250,000 CPM. As the viral load increased through day 10, label incorporation rose to approximately 350,000 CPM. After day 10, cell death as a result of HIV-1 infection resulted in a dramatic decrease in activity.

The presence of cationized anti-Tat #3 in the growth media resulted in a dramatic decrease in reverse transcriptase activity. For example, on day 10 at the peak of infection, the activity levels shown on Curve C (anti-Tat #3) represent a level of label incorporation which is about 70–80% less than that shown on control curves A and B.

Example 2

In order to determine the degree of cationization which is sufficient to induce intracellular delivery, the anti-Tat monoclonal antibody discussed in the previous Example was cationized using the diamine putrescine. The cationization reaction was carried out in a 500 µl reaction mixture consisting of 100mM MOPS buffer (pH 7.2); 10% glycerol; 400 µg anti-Tat; 125µmoles putrescine; $7.26\times10^6$ cpm $^3$H-putrescine; and 1 µmole EDC (carbodiimide). The reaction was maintained at room temperature for about 20 hours.

The cationized anti-Tat antibody was then separated from excess putrescine and EDC by chromatography on a PD-10 column. The number of putrescines per antibody was calculated from the amount of antibody recovered and the incorporated radioactivity, and was estimated to be about 9.05. The affinity of the cationized antibody for the Tat protein was assessed by an ELISA binding assay as discussed previously. It was determined that the modified antibody had retained about 15% of its affinity for Tat.

This anti-Tat preparation was tested on HIV-1 infected cells in vitro. More specifically, Sup T1 cells were cultured in 24 well plates (2 ml volumes, 200,000 cells per well). From day 0 through day 5, the cell culture media was replaced daily with fresh media containing either no antibody, or the anti-Tat antibody in its native form, or cationized as described above (approximately 10µg/ml). On day 1, cells to be infected were exposed to an HIV-1 IIIB preparation under conditions appropriate for infection. Cell counts were taken daily. From day 6 through 10, the culture media was replaced daily with fresh media without added antibody.

Figure 2:
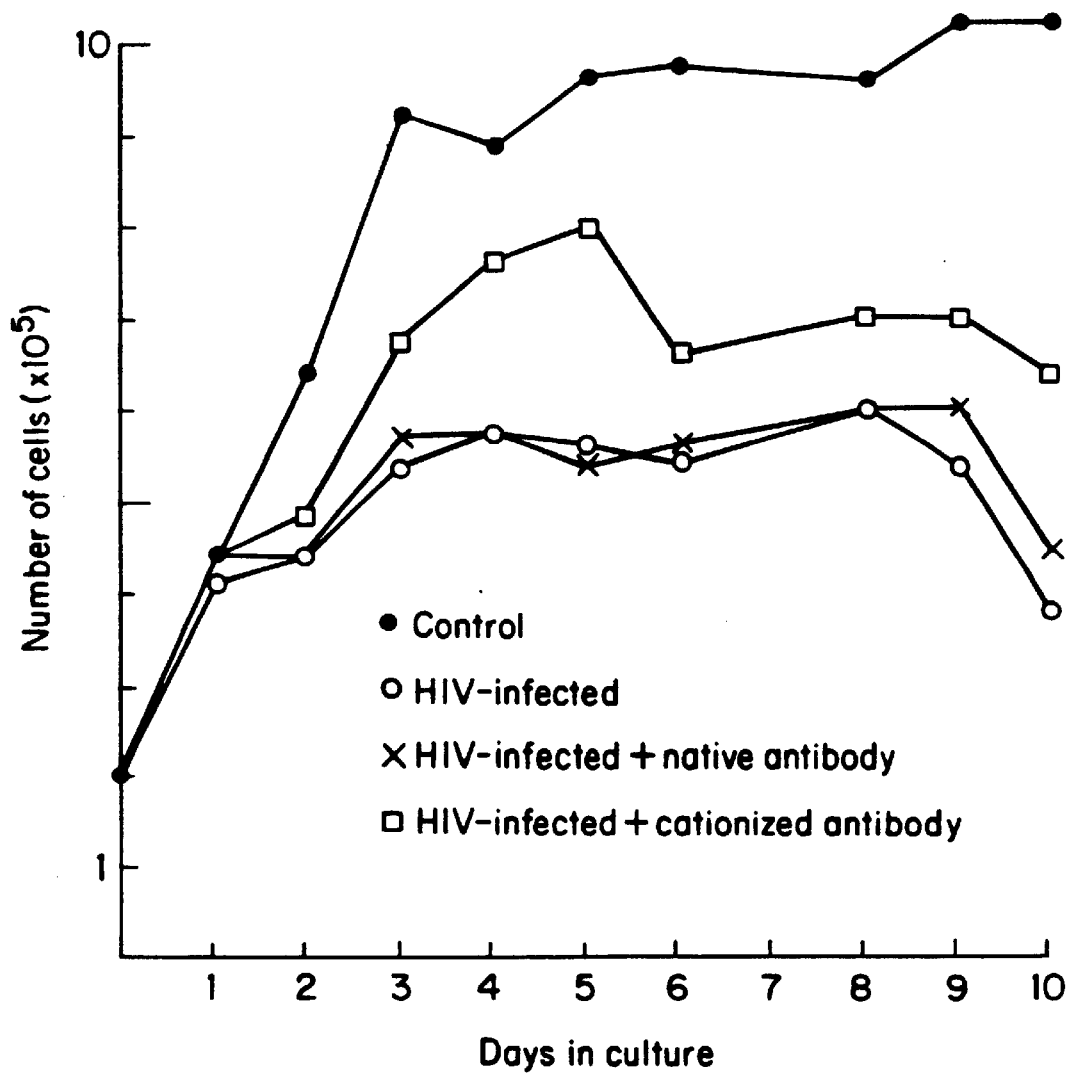
FIG. 2 is a diagram representing results from experiments testing the effect of cationized anti-Tat on the viability of virus infected cells.

FIG. 2 shows cell counts over time (from day 0 up to day 10). While Sup T1 cells maintained without antibody and not infected with the virus reached a density of about one million cells per well, when infected with the virus the cells only reached about half this density, and after day 8, the cell count per well began to drop due to the cytopathic effect of the virus. While the native anti-Tat antibody had no effect, the cationized antibody induced an increase in cell density which was particularly marked until day 5. From day 6 to day 10 (when the cells were incubated without any added antibody), cell density decreased but remained higher than that for untreated, infected cells or infected cells treated with the native antibody.

Equivalents

Those skilled in the art will know, or be able to ascertain using no more than routine experimentation, many equivalents to the specific embodiments of the invention described herein. These and other equivalents are intended to be encompassed by the following claims.

What is claimed is:

1. A method for targeting an intracellular protein in a cell comprising contacting said cell with a cationized antibody which thence enters said cell and immunologically binds with said intracellular protein.

2. A method of claim 1 wherein the cationized antibody is labeled with a detectable reporter group.

3. A method of claim 2 wherein the reporter group is a fluorescent moiety.

4. A method for inhibiting the activity of an intracellular protein in a cell comprising contacting said cell with a cationized antibody which immunologically binds with said intracellular protein thereby inhibiting the activity of said intracellular protein.

5. A method of claim 4 wherein the cationized antibody is a monoclonal antibody.

6. A method of claim 4 wherein the intracellular protein is a trans-activating protein.

7. A method of claim 6 wherein the trans-activating protein is a protein which binds to nucleic acid in the cell.

8. A method of claim 7 wherein the trans-activating protein is the HIV-1 Tat protein.

9. An immunotherapeutic method for treating an individual infected by a virus comprising administering to said individual an effective amount of homologous cationized antibody which immunologically binds with a virus encoded product thereby interfering with replication of said virus.

10. A method of claim 9 wherein the virus is selected from the group consisting of DNA viruses and retroviruses.

11. A method of claim 10 wherein the retroviruses are lentiviruses.

12. A method for treating an individual infected by the HIV-1 virus comprising administering to said individual an effective amount of a homologous cationized antibody which immunologically binds with an HIV-1 encoded trans-activating factor thereby reducing the reverse transcriptase activity associated with said HIV-1 virus.

13. A method of claim 12 wherein the HIV-1 encoded trans-activating factor is the Tat protein.

14. A method of claim 13 wherein the cationized antibody is a monoclonal antibody.

15. A method of claim 12 wherein the HIV-1 encoded trans-activating factor is the Rev protein.

* * * * *